United States Patent [19]

Rubel et al.

[11] 4,080,562

[45] Mar. 21, 1978

[54] APPARATUS FOR MEASURING CAPACITANCE OR RESISTANCE AND FOR TESTING A CAPACITANCE RESPONSIVE GAGING SYSTEM

[75] Inventors: Ira A. Rubel, Smithtown; Herbert A. Steiner, Whitestone; Charles H. Ritter, Ronkonkoma, all of N.Y.

[73] Assignee: Gull Airborne Instruments, Inc., Smithtown, N.Y.

[21] Appl. No.: 670,141

[22] Filed: Mar. 25, 1976

[51] Int. Cl.² .................................................. G01R 27/00
[52] U.S. Cl. .............................. 324/57 R; 324/60 C; 324/62; 324/73 R
[58] Field of Search ............... 324/57 R, 60 C, 62, 324/73 R; 73/304 C

[56] References Cited

U.S. PATENT DOCUMENTS

B 540,218   2/1976   Thomas ............................ 324/60 C
3,830,090   8/1974   Hersch et al. .................. 73/304 C X
3,992,665   11/1976  Preikschat ........................ 324/57 R Primary Examiner—Stanley T. Krawczewicz

[57] ABSTRACT

This apparatus includes means for measuring capacitance or resistance and means for simulating a selected capacitance value. The apparatus is connectible into a fuel gaging system. When so connected, a selector switch can be operated to make the normal connections between the fuel gaging capacitors and the indicators, so that the indicators produce their normal responses. Alternatively, the selector switch may be operated so that the apparatus measures the capacitance or resistance of various elements in the gaging system. As another selection, a simulated value of capacitance may be inserted in the gaging system to make the indicators in that system respond to the simulated value in addition to the capacitance of the fuel gaging capacitors of the gaging system.

8 Claims, 8 Drawing Figures

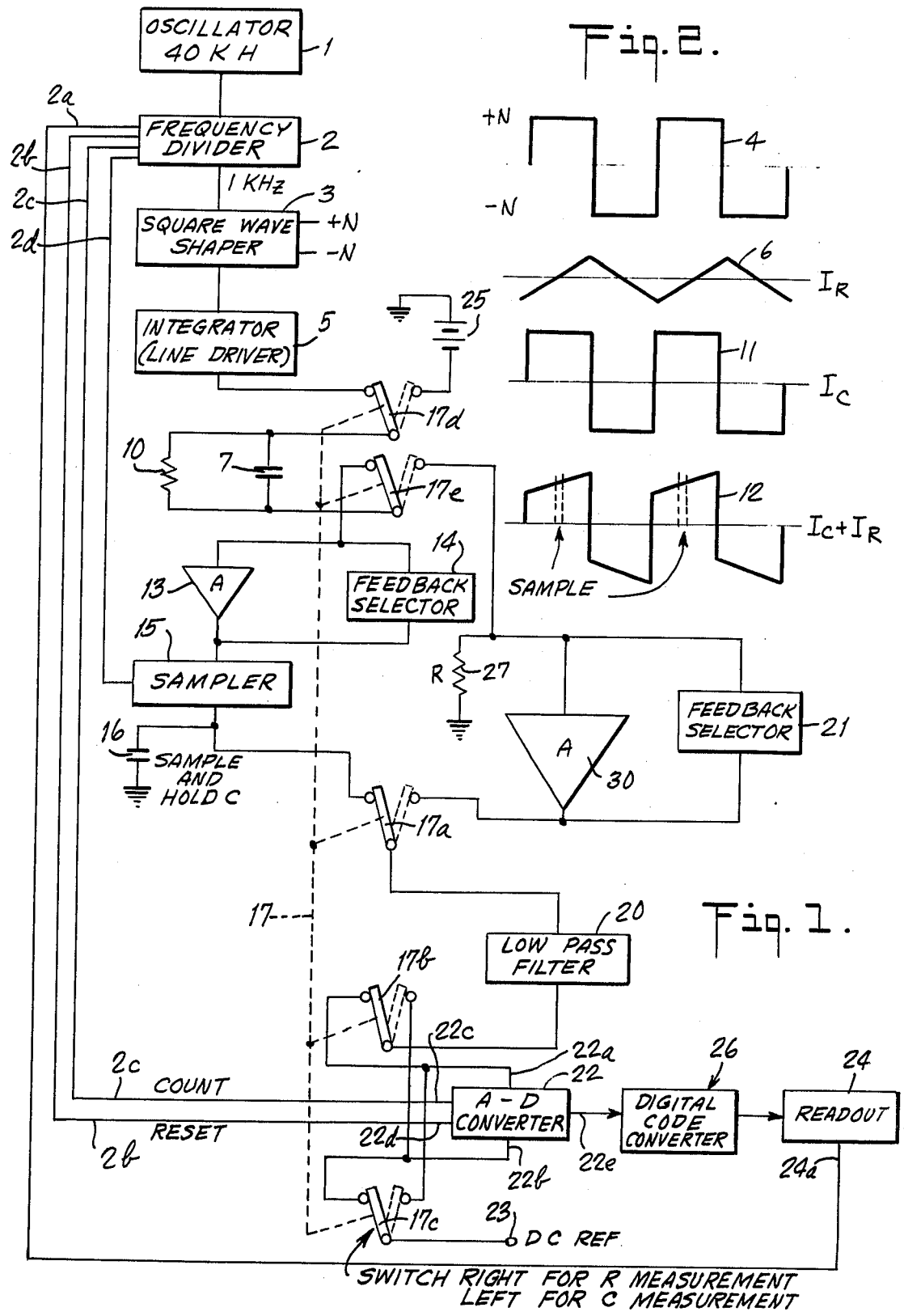

APPARATUS FOR MEASURING CAPACITANCE OR RESISTANCE AND FOR TESTING A CAPACITANCE RESPONSIVE GAGING SYSTEM

CROSS-REFERENCE

This apparatus is particularly intended for the measurement of capacitance and resistance values and the simulation of capacitance in fuel gaging systems, such as, for example, the system shown in U.S. Pat. No. 3,830,090, issued to Hersch and Rubel on Aug. 20, 1974, although it is suitable for making other capacitance and resistance measurements.

BRIEF SUMMARY

The capacitance and resistance measuring apparatus includes an analog-to-digital converter which operates either in a capacitance measuring mode or a resistance measuring mode. Resistance is measured directly by conducting a direct current at a constant potential through the resistor under test. The potential drop across a known resistor in series with the resistor under test is supplied to the divisor input of the converter and a reference potential is supplied to the dividend input of the converter, thereby producing a digital output inversely proportional to the current and hence directly proportional to the resistance. Capacitance is measured by impressing a triangular alternating potential wave across the capacitor under test. Such a wave is integrated by the capacitor so that the current flow through the capacitor is a square wave. The wave of current flow through a resistor in parallel with the capacitor (e.g., the dielectric leakage resistance) is triangular like the impressed potential. The sum of these current waves is sampled at the midpoint of one half of each cycle, at which points the current sum is a direct measure of the capacitance. This sampled voltage is stored on a holding capacitor. The potential there is supplied to the dividend input of the converter while the reference potential is applied to the divisor input, thereby providing a readout directly proportional to the capacitance of the capacitor. Switch means is operable to select either the capacitance measuring mode or the resistance measuring mode.

The test set is adapted for connection in an aircraft fuel gaging system which includes a fuel level measuring capacitor, a fuel density compensating capacitor, indicator means and means responsive to a function of the capacitances of the two capacitors for operating the indicating means.

The test set includes first and second simulating capacitors, which are manually variable and which may be set to preselected values corresponding to those of the fuel measuring and compensating capacitors. An eight-position selector switch has four positions in which the capacitance measuring apparatus is set to measure, one at a time, the two capacitors in the gaging system and the two simulating capacitors in the test set. A fifth position of the selector switch connects the fuel measuring and compensating capacitors to the indicating means in their normal operating connections. A sixth position of the selector switch connects the first and second simulating capacitors of the test set to the indicator means. A seventh position of the selector switch connects the fuel measuring capacitor and one simulating capacitor in parallel to the indicator means and also connects the compensating capacitor and the other simulating capacitor in parallel to the indicator means. An eighth position connects the measuring capacitor and the first simulating capacitor in parallel to the indicator operating means with only the compensating capacitor connected in that network, omitting the second simulating capacitor.

These eight positions of the selector switch enable a complete testing, troubleshooting and calibration of a fuel gaging system after making one interconnection of the test set and the system.

DRAWINGS

FIG. 1 is a block diagram of capacitance and resistance measuring apparatus constructed in accordance with the invention.

FIG. 2 is a graphical illustration of potentials and currents occurring in the apparatus of FIG. 1.

DETAILED DESCRIPTION

CAPACITANCE MEASUREMENT

Figure 3:
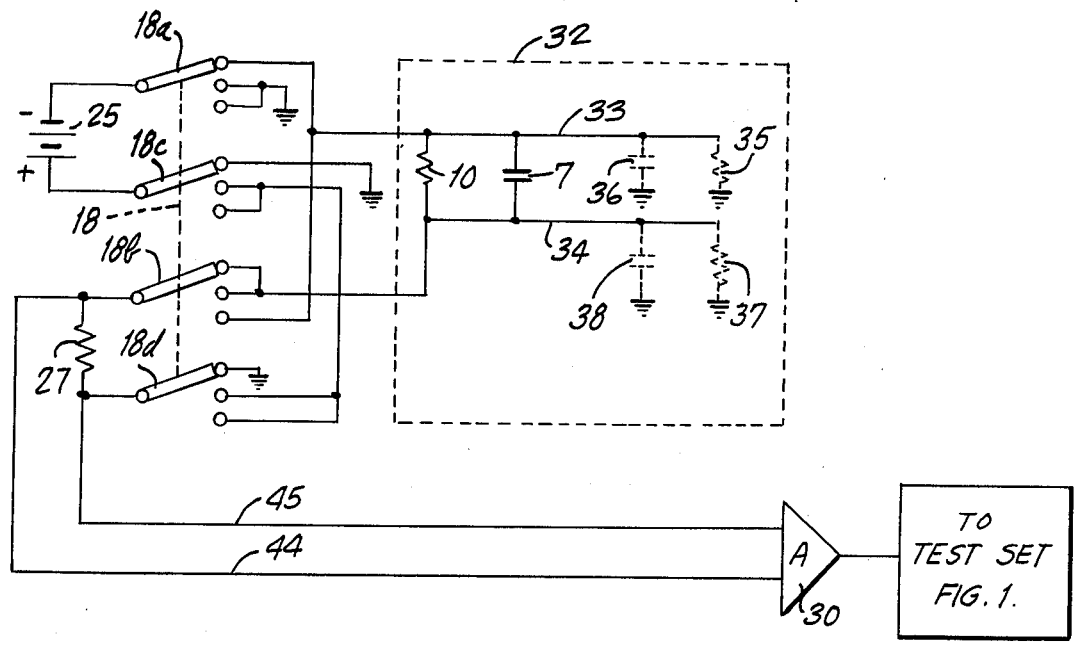
FIG. 3 illustrates the connection of the apparatus of FIG. 1 to measure a selected resistor or capacitance while the measured element is connected to other circuit components.

The apparatus of FIG. 1 is supplied with power for purposes of capacitance measurement and also for certain functions of resistance measurement by an oscillator 1, which may, by way of example, have a frequency of 40KHz. The output of oscillator 1 is supplied to a frequency divider 2 whose principal output for driving the capacitance measurement circuit may operate at 1KHz. The frequency divider 2 also has four other outputs identified as 2a, 2b, 2c, and 2d, operating at various frequencies, as described below. The 1KHz. output of the divider 2 is supplied to a square wave shaper 3 which produces a 1KHz. output having a wave form as shown at 4 in FIG. 2. The square wave shaper 3 may have connections to a pair of fixed voltage sources having potentials of +N and −N, respectively, which limit the contours of the tops and bottoms of the output wave. It is not necessary that the positive and negative excursions of the wave be symmetrical.

The output of wave shaper 3 is supplied to an integrator circuit 5 whose output is a potential having the shape of a triangular wave 6, shown in FIG. 2. A switch 17 has a capacitance measuring position, shown in full lines in the drawing, and a resistance measuring position, shown in dotted lines. Switch 17 has five contact fingers 17a, 17b, 17c, 17d, 17e. When switch 17 is in its capacitance measuring position, the triangular potential wave is impressed across a capacitor 7 under test through switch fingers 17d and 17e. A resistor 10, connected in parallel with capacitor 7, represents the resistance of the dielectric between the electrodes of that capacitor. That dielectric resistance, in the circuits for which this set is intended, is in the megohm range, e.g., from one-tenth to 100,000 megohms.

The current flow through the capacitor 7 is a differentiation of the applied voltage and hence is a square wave 11 displaced 90° in phase from the voltage wave 6, as shown in FIG. 2. The current through the resistor 10, on the other hand is in phase with the applied voltage and hence has a triangular wave form as shown at 6. The sum of the currents 6 and 11 has a contour as shown at 12 in FIG. 2 and is transmitted through an amplifier 13 having a feedback selector 14 to a sampler circuit 15 controlled by output 2d of the frequency divider 2. Feedback selector 14 acts as a range selector, i.e., it determines the output from amplifier 13 for a given input.

The feedback selector 14 may be simply a selector switch arranged to connect a selected one of several resistors having different resistances in the gain control circuit of the amplifier 13.

At the midpoint of each positive half cycle of the current wave 12, its amplitude is a measure of the capacitor current 11, since at that instant the resistor current 6 is passing through zero. Hence, by sampling the positive half cycles of the wave 12 at the midpoints, a potential is obtained which is a measure of the capacitance of capacitor 7 and is not affected by the resistance 10. Furthermore, sampling at the midpoint of the half cycle avoids transient oscillations which might occur at the beginning of the half cycle. For a 1000Hz. wave such as shown at 12, it has been found suitable to use a sampling interval of 1/30th of the duration of a cycle. A 1000Hz. wave has a period of 0.001 second. The sampling interval may then be taken as 0.000033 second, or shorter if desired. The sample potential passed by sampler 15 is transferred to a capacitor 16. Since a sample reaches the capacitor 16 on every positive half cycle, those samples are stored and held on capacitor 16.

Although the positive half cycles have been selected for sampling in the apparatus as shown, an acceptable alternative would be to use the negative half cycles instead. It is obvious that both positive and negative half cycles could not be used since their effects would cancel out at the holding capacitor 16.

When switch 17 is in the capacitance measuring position the potential appearing on the holding capacitor 16 is transmitted through contact 17a to the input of a low pass filter 20, and thence through contact 17b of switch 17 to a dividend input 22a of an analog-to-digital converter 22. A DC reference potential is supplied from a suitable source 23 though contact 17c to a divisor input 22b of converter 22. Converter 22 receives counting pulses at a count pulse 22c from output 2c of the frequency divider 2 and reset pulses at an input 22d from output 2b of the frequency divider.

It is known in the art that an analog-to-digital converter of suitable construction produces a digital output which is a measure of the quotient of an analog input signal divided by a reference input signal. See, for example, the U.S. Pat. to Palevsky et al, No. 3,077,303, issued Feb. 12, 1963, column 4, lines 13–32, column 12, lines 66–72, and column 25, line 73 to column 26, line 6.

The converter 22 is of the discrete voltage comparison type. After each reset pulse, the converter starts counting the pulses at the count input 22c and passes the count to its digital output 22e. The digital output continues to increase until that output, reconverted to analog form, balances the dividend input 22a. Each count at the digital output produces a predetermined increment of balancing potential. Each increment has a preselected ratio with the reference potential at the divisor input 22b. After reaching an output which balances the input at 22a, the converter 22 holds that output until the next reset pulse is received at 2d. The counting time required is short as compared to the time between reset pulses, so that the conversion process may be completed.

It is also known in the art to construct an analog-to-digital converter which starts each new conversion in response to a cyclically repeated reset pulse. See, for example, the U.S. Pat. to Schumann, No. 3,811,125, showing a converter in which each conversion is started by a signal delivered to an initiate conversion terminal 14. The digital output 22e is supplied to a digital code converter 26 which feeds a readout 24. Readout 24 gives a digital indication, in plural digital orders, of the value of the capacitance of capacitor 7, unaffected by resistance (e.g., the dielectric leakage resistance) in parallel with it.

RESISTANCE MEASUREMENT

To measure resistance, the switch 17 is shifted from the position shown in full lines in the drawing to the dotted line position. Switch fingers 17d and 17e are moved from the capacitance-measuring position shown in FIG. 1 to the resistance-measuring position, thereby connecting one terminal of resistor 10 to a fixed voltage source 25, whose opposite terminal is grounded. A fixed resistor 27 of known resistance is connected in series with the resistor 10 under test. The resistor 27 is chosen to be very small as compared to the resistor 10 under test so that the current flow through resistor 27 is determined, within the desired limits of accuracy, by the resistance of resistor 10 alone. The potential drop across resistor 27, which is a measure of that current, is supplied to the input of an amplifier 30, whose output is connected to a stationary contact now engaged by the movable contact 17a of switch 17, thence through the low pass filter 20 to movable contact 17b, and thence to the divisor input 22b of the converter 22. A feedback selector 21 is connected between the output and input terminals of the amplifier 30, and serves as a range adjustment. The DC reference potential at 23 is now connected through contact 17c to the dividend input 22a of converter 22. Consequently, the converter 22 now produces an output which is inversely related to the current flow through resistor 10, and hence is a direct measurement of the resistance of that resistor.

The readout 24 is measuring a ratio between two voltages in which the smaller voltage (reference potential) is divided by the larger voltage (representing the IR drop across the resistor 10). The readout appears as a decimal value and the range of the readout (four or five decimal orders) is relatively small as compared to the range of resistances which may be tested. Since the apparatus may be used to measure resistances over a range from one-tenth to 100,000 megohms, the resistors under test may vary, from one to the next, by more than the number of decimal orders in the readout.

The readout 24 is supplied with a flasher input 24a receiving flasher pulses from output 2a of the frequency divider 2. The readout 24 is connected to activate the flasher input and produce a flashing signal, whenever all of the digit indicators of the readout are either in their maximum or minimum condition. In other words, when the flashing signal occurs, a range adjustment should be made by means of the feedback selector 21, to change the significance of the digits appearing in the readout so as to make an intelligible measurement.

FIGS. 3 AND 4

These figures illustrate the measurement of a resistor while it remains connected in an operating system, such as the fuel measuring system shown in the Hersch et al U.S. Pat. No. 3,830,090, mentioned above. There are shown in a chain line box 32 in this figure the fuel measuring capacitor 7, and the resistor 10, connected in parallel with capacitor 7 and representing the resistance of the dielectric between the plates of the capacitor. The capacitor 7 is connected between conductors 33 and 34 which extend to a remotely located indicating system. A resistor 35, shown dotted, represents the distributed insulation resistance between conductor 33 and ground. A capacitor 36, also shown dotted, represents the distributed capacitance between the conductor 33 and ground. Similarly, a resistor 37 and a capacitor 38 represent the distributed resistive and capacitive paths between line 34 and ground.

When the test set of FIG. 1 is connected to measure the resistance 10 in parallel with capacitor 7, the source of direct potential 25 and resistor 27 are connected in series with the resistor 10 through the contacts of a switch 18. See FIG. 3. This series connection may be traced from ground through contact 18c, source 25, contact 18a, resistor 10, contact 18b, resistor 27, and contact 18d back to ground. Amplifier 30 has an input terminal connected to the common junction of resistors 27 and 10.

Since the resistance of resistor 10 is measured with direct current, the distributed capacitances 36, 38 and the capacitor 7 have no effect on the measurement after a steady state of current flow through the circuit has been established.

As described in connection with FIG. 1, the amplifier 30 in measuring the current flow through the known resistor 27, which has a resistance much smaller than that of the resistor 10. Resistors 35 and 37 are of the same order of magnitude at resistor 10. Since resistor 37 is shunted by resistor 27, and the latter is much smaller, the current flow through resistor 37 may be reduced to a value where it is not significant within any desired limits of accuracy by suitably proportioning resistor 27.

Figure 4:
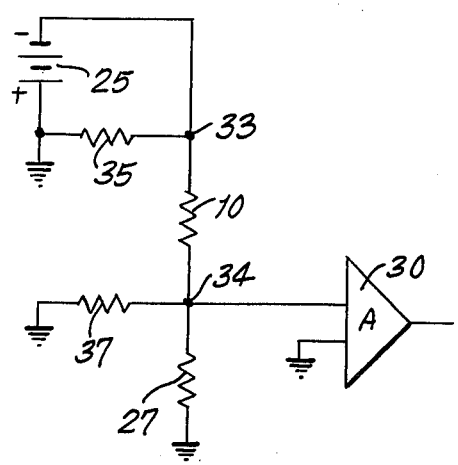
FIG. 4 is a simplification of the circuit of FIG. 3, for the purpose of illustrating the relationships therein when used to measure a particular resistor.

Resistor 35 is connected in parallel with the source 25, so that its resistance does not affect the current flow through the resistor 27. Hence, the current flow though resistor 27 may be taken as inversely proportional to the resistance of resistor 10. Thus, a potential varying inversely with the resistance of resistor 10 is supplied to the amplifier 30 to be measured and read by converter 22 and readout 24, as in FIG. 1. See FIG. 4, which illustrates the connections described above with all capacitors and switch contacts omitted.

FIGS. 5 AND 6

These figures illustrate the connection of the apparatus to measure the insulation resistances 35 and 37 in the fuel gaging system of the Hersch et al U.S. Pat. No. 3,830,090. The circuit configuration of FIG. 5 measures the resistance of two parallel branches, one including only resistor 37, the other including resistors 10 and 35 in series. To measure that resistance, switch 18 of FIG. 3 is moved from the position shown to one in which each of the switch fingers engages the middle one in its associated array of three stationary contacts. The upper terminal of battery 25 is then connected through contact 18a to ground. The lower terminal of battery 25 is connected through contacts 18c, 18d and a conductor 45 to one input of the amplifier 30. The other input of amplifier 30 is connected through a conductor 44 and contact 18b to the line 34.

Figure 5:
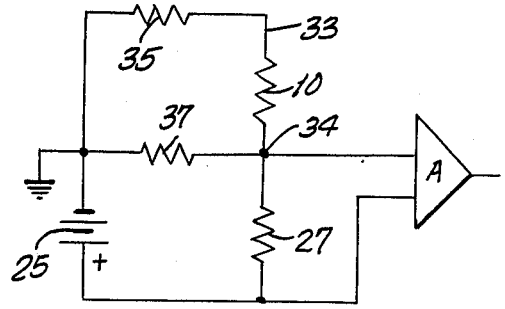
FIGS. 5 and 6 are similar simplifications of FIG. 3, illustrating the measurement of other particular resistance elements.

With the switches and the capacitors omitted, the circuit of FIG. 3 with switch 18 in its middle position becomes the circuit shown in FIG. 5, where it may be seen that the amplifier 30 is connected across the fixed resistor 27. The resistors 35 and 37 are permanently connected between the respective terminals of resistor 10 and ground.

Since resistance 27 is much smaller than the resistors 10, 35 and 37, its effect on the current flow through those resistors and hence on the voltage drop across resistor 27 is relatively small and may be ignored. The circuit of FIG. 5 is measuring the resistance of a parallel combination containing in one parallel branch, the resistors 10 and 35 in series and in another parallel branch the resistor 37 alone.

Figure 6:
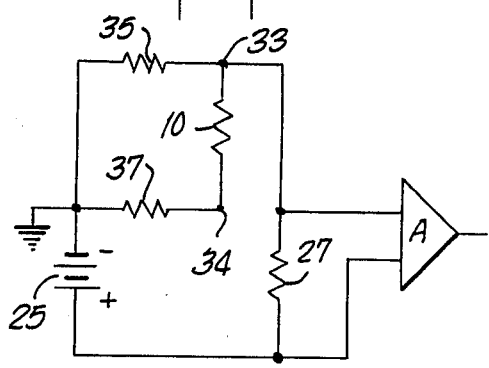

By throwing the switch 18 to the lower position in FIG. 3 the connections of resistor 27 and source 25 will be changed from those shown in FIG. 5 to those shown in FIG. 6. Here the circuit measures the resistance of two parallel branches, one containing resistor 35 alone, and the other containing resistors 10 and 37 in series. Since resistor 10 may be separately measured, as shown in FIG. 1, it is possible to determine each of the resistances 10, 35 and 37 by measuring the resistance of resistor 10 separately and then making the two measurements of FIGS. 5 and 6. In other words, the measurements are made with the switch 18 first in the upper position and then in the middle and lower positions. The resistance of each of the resistors 35 and 37 may be computed mathematically from the results of these measurements.

FIGS. 7 AND 8

Figures 7, 8:
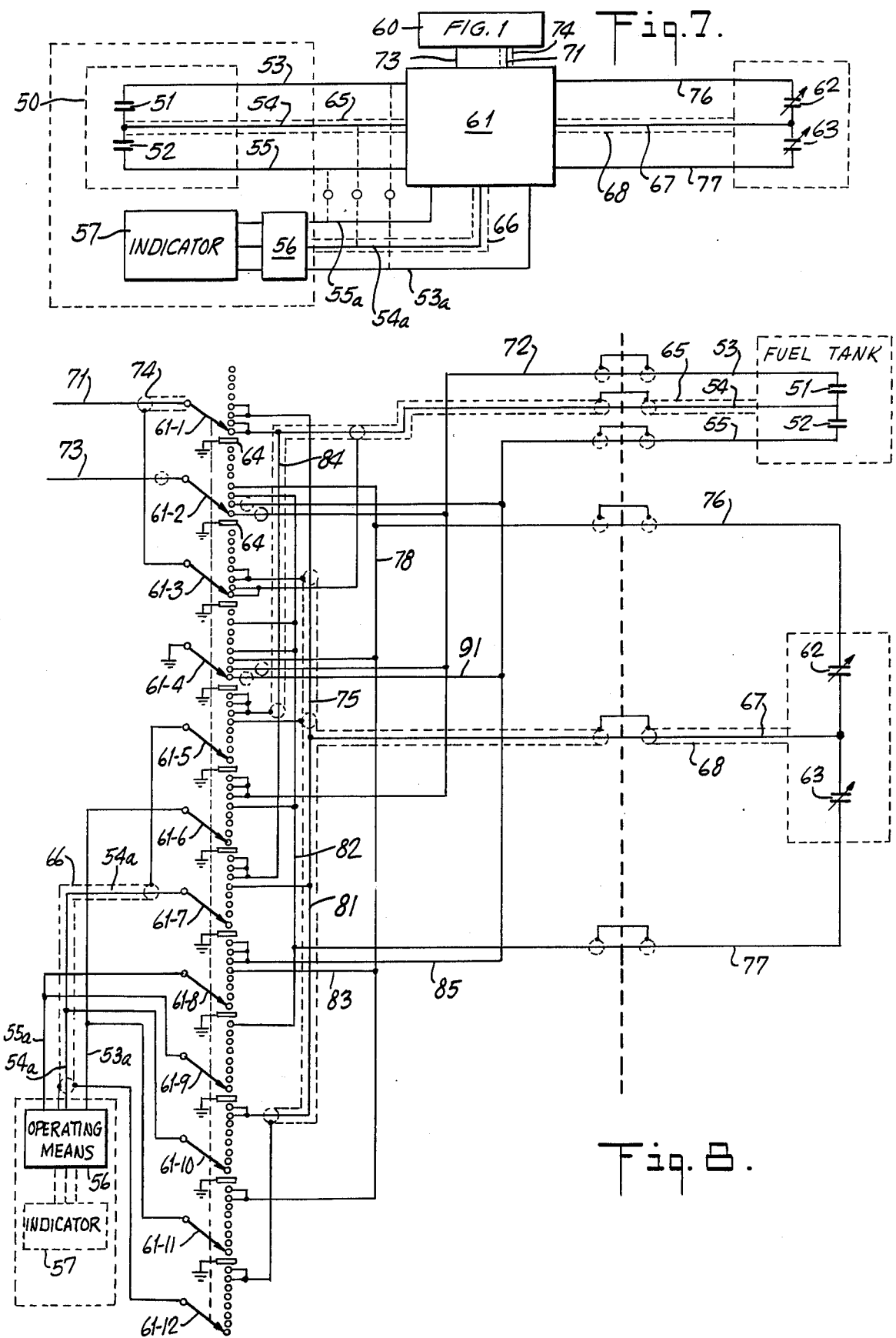
FIG. 7 is a block diagram of a fuel gaging system, with apparatus connected thereto for testing that system in accordance with the invention.
FIG. 8 is a wiring diagram of a selector switch in the apparatus of FIG. 7.

FIG. 7 shows in block diagram form a test set constructed in accordance with the invention connected to a capacitance fuel gaging system which may be either of those shown in Hersch et al, U.S. Pat. No. 3,830,090, mentioned above and Horowitz, U.S. Pat. No. 3,801,902, issued Apr. 2, 1974.

A fuel gaging system such as those disclosed in the Hersch et al and Horowitz patents includes, for each fuel tank, a fuel measuring capacitor 51 and a density compensating capacitor 52. These capacitors are connected by conductors 53, 54 and 55 to an operating means 56 which drives an indicator 57. A complete system such as those shown in the Hersch et al and Horowitz patent includes several fuel tanks, each of which has an array of one or more fuel measuring capacitors 51 and one or more density compensating capacitors 52. Furthermore, there may be indicators 57 at more than one location for each fuel tank. However, in the interest of simplicity, only one fuel measuring capacitor 51, one compensating capacitor 52 and one indicator 57 are illustrated.

The apparatus of the present invention includes a capacitance and resistance measuring unit, such as that illustrated in FIG. 1 and shown at 60 in FIG. 7, a function selector switching unit shown at 61 and illustrated in detail in FIG. 8, and a pair of simulating capacitors 62 and 63. The simulating capacitors 62 and 63 are connected to the switching unit 61 through conductors 76, 67 and 77. The simulating capacitors 62 and 63 are manually variable. The simulating capacitors, the switching unit 61 and the resistance and capacitance measuring unit 60 may conveniently be constructed as a single portable unit.

When the fuel gaging system is operated normally, its conductors 53, 54, 55 are connected through dotted line connections shown to conductors 53a, 54a, 55a, respectively, leading to indicator operating means 56. When the test apparatus of the present invention is applied to the fuel gaging system then those dotted lines connections are interrupted. The conductors 53, 54 and 55 leading to the capacitors 51 and 52 are then connected to the switching unit 61, as are the conductors 53a, 54a, and 55a, connected to the indicator driving means 56.

The switching unit 61, as shown in detail in FIG. 8, has twelve movable contacts numbered respectively 61-1 to 61-12. Each of the movable contacts 61-1 to 61-12 cooperates with eight stationary contacts. The twelve movable contacts are all mechanically ganged together so that they are operated simultaneously by an appropriate manual operator. Thus, the switch has eight operating positions. In the following description, the position in which the movable contacts engage the lowest stationary contacts, as they appear in the drawing, is identified as the first position and the position in which the movable contacts engage the uppermost contacts is identified as the eighth position. The other positions are numbered sequentially between the first and eighth.

The contacts 61-1 to 61-12 are all shielded from each other by appropriate shields, shown diagrammatically in the drawing at 64. The conductors 54 and 54a are provided with shields 65 and 66, respectively. The conductors 54 and 54a must be electrostatically shielded with respect to conductors 53, 55, 53a and 55a to eliminate interwiring capacitance, which would produce erroneous measurement. The conductor 67 connected to the common terminal of the simulating capacitors 62 and 63 is similarly provided with a shield 68 to prevent erroneous simulation.

When the switch 61 is in its first position, as illustrated in FIG. 8, the conductor 54 leading from the common junction of the capacitors 51 and 52 is connected through switch contact 61-1 to a conductor 71 leading to the capacitance and resistance measuring unit 60. The upper terminal of capacitor 51 is connected through conductors 53 and 72 and switch contact 61-2 to a conductor 73, also leading to the capacitance measuring unit 60. The conductor 71 is shielded as indicated at 74. The shield 65 around conductor 54 and shield 74 around conductor 71 are connected through the switch contact 61-3. The fuel measuring capacitor 51 is connected to the capacitance measuring unit 60 in the position shown for the capacitor 7 and its parallel dielectric resistance 10 in FIG. 1. The measuring unit 60 is thereby connected to measure the capacitance of the capacitor 51. The lower terminal of capacitor 52 is connected through conductor 55 and 91 and switch contact 61-4 to ground.

The other contacts (61-5 to 61-12) of switch 61 are not employed in the first four positions of the switch 61.

In the second position of switch 61, conductor 54 and its shield 65 are connected to conductor 71 and its shield 74, as in the first position. However, the lower terminal of the compensating capacitor 52 is now connected through contact 61-2 to conductor 73. The upper terminal of capacitor 51 is connected to ground through contact 61-4. Consequently, in the second position of the switch 61, the measuring unit 60 is connected to measure the capacitance of capacitor 52.

In the third position of switch 61, the common terminal of the capacitors 62 and 63 is connected through conductors 67 and 75 and contact 61-1 to conductor 71 and thence to the measuring unit 60. The shield 68 is connected through contact 61-3 to the shield 74. The lower terminal of the simulating capacitor 63 is connected through conductors 77 and 82 and contact 61-2 to conductor 73 and thence to the measuring unit 60. The upper terminal of capacitor 62 is grounded through contact 61-4. The measuring unit is now connected to measure the capacitance of simulating capacitor 63.

In the fourth position of switch 61, the upper terminal of simulating capacitor 62 is connected through conductors 76 and 78 and switch contact 61-2 to conductor 73. The connections through contacts 61-1 and 61-3 remain as in the third position. The lower terminal of capacitor 63 is grounded through contact 61-4. The measuring unit 60 is now connected to measure the capacitance of simulating capacitor 62.

In the fifth position of switch 61, only contacts 61-5 to 61-8 are employed. The common terminal of the simulating capacitors 62 and 63 is connected through conductors 67 and 75, contact 61-7 and conductor 54a to the operating means 56 for indicator 57. The lower terminal of capacitor 63 is connected through conductors 77 and 82, contact 61-6, and conductor 53a to the operating means 56. The upper terminal of simulating capacitor 62 is connected through conductors 76 and 78, switch contact 61-8, and conductor 55a to the indicator operating means 56. The shield 68 is connected through contact 61-5 to shield 66. The system is then set so that the indicator 57 reads a value determined by the setting of capacitors 62 and 63. If the capacitances of those two capacitors have already been measured by the use of the third and fourth positions of switch 51, then this fifth position of switch 61 tests the accuracy of the indicator 57. When this test is made, i.e., when switch 61 is in the fifth position, the indicator operating means 56 is disconnected from capacitors 51 and 52 of the fuel gaging system.

In the sixth position of switch 61, the common terminal of capacitors 51 and 52 is connected through conductors 54 and 84 and switch contact 61-7 to conductor 54a and thence to the operating means 56. Shield 65 is at this time connected through contact 61-5 to shield 66. The upper terminal of the capacitor 51 is connected through conductors 53 and 72, switch contact 61-6 and conductor 53a to the operating means 56. The lower terminal of capacitor 52 is connected through conductors 55 and 85, contact 61-8 and conductor 55a to the operating means 56. The tank capacitors 51 and 52 are now connected to the indicator operating means 56 in the same way as they would be connected in normal operation. This connection is used to set the empty indication of indicator 57, using the actual capacitor units of the fuel gaging system.

In the seventh position of the switch 61, the common terminal of capacitors 51 and 52 is connected through conductors 54 and 84 and contact 61-7 to conductor 54a as it was in the sixth position, above. The common terminal of capacitors 62 and 63 is connected through conductors 67 and 81 and contact 61-10 to the same conductor 54a. The shield 65 around conductor 54 is connected through contact 61-5 to shield 66. Shield 68 around capacitor 67 is connected through contact 61-12 to shield 66. The upper terminal of capacitor 51 is connected through wires 53 and 72 and switch contact 61-6 to conductor 53a. The upper terminal of capacitor 62 is connected through conductors 76 and 78 and contact 61-11 to conductor 53a. The lower terminal of capacitor 52 is connected through conductors 55 and 85 and contact 61-8 to conductor 55a. The lower terminal of capacitor 63 is connected to conductors 77 and 82 and contact 61-4 to ground. Hence, the level measuring capacitor 51 is connected in parallel with the simulating capacitor 62 across conductors 53a and 54a leading the operating means 56. Only the capacitor 52 is connected between the conductors 54a and 55a. This setting of the switch 61 allows establishment of a value for the "tank full" reading of the indicator 57. The simulating capacitor 62 is set to represent the difference between the dry reading and the full reading of the tank capacitor. This test is made in the seventh switch position only when the tank is dry except that the compensating capacitor 52 is immersed in fuel. The compensating capacitor is located at the lowest point in the fuel tank. Typically, after a tank has been in use, the compensating capacitor is thereafter always wet with fuel, even though the tank is nominally empty. It is therefore not necessary to add any capacitance to the compensating capacitor 52 to correct for the dry tank condition.

In the eighth position of the switch 61, the capacitors 51 and 62 are connected in parallel between conductors 53a and 54a and capacitors 52 and 63 are connected in parallel between conductors 54a and 55a. The connection between conductors 54 and 54a is through switch contact 61-7. The connection between conductors 67 and 54a is through switch contact 61-10. The connection between conductors 53 and 53a is through contact 61-6. The connection between conductors 55 and 55a is through contact 61-8. The connection between conductors 76 and 53a is through switch contact 61-11. The connection between conductors 77 and 55a is through switch contact 61-9. Shield 68 is connected to shield 66 through contact 61-12. Shield 65 is connected to shield 66 through contact 61-5.

Capacitor 62 represents an increment of capacitance to be added to the capacitance of fuel measuring capacitor 51. Capacitor 63 represents an increment of capacitance to be added, for certain tests, to the capacitance of compensating capacitor 52.

The eighth position is used to set the indicator to read full when the tank is completely dry, as in a newly constructed fuel system. Each simulating capacitor is set to a value designed to equal the increase in capacitance expected between the completely dry (air dielectric) and completely full (fuel dielectric) conditions.

The various shield connections eliminate the interwiring capacitance between conductors.

We claim:

1. Apparatus for selectively measuring either the capacitance of a capacitor or the resistance of a resistor, comprising:
   (a) an analog-to-digital converter having a divisor analog input, a dividend analog input, and a quotient digital output;
   (b) means for producing a first electrical analog potential varying directly with said capacitance;
   (c) means for producing a second electrical analog potential varying inversely with said resistance;
   (d) a source of fixed electrical reference analog potential; and
   (e) switch means operable between:
      (1) a first condition in which said first potential is connected to said dividend input and said reference potential is connected to said divisor input so that the converter produces at the quotient output a digital signal varying directly with said capacitance, and
      (2) a second condition in which said second potential is connected to said divisor input and said reference potential is connected to said dividend input, so that the converter produces at the quotient output a digital signal varying directly with said resistance.

2. Apparatus as in claim 1, in which said converter has a digital counting pulse input and a reset pulse input, said apparatus including:
   (a) an oscillator having a high frequency pulse output connected to said digital counting pulse input; and
   (b) a frequency divider driven by said oscillator for supplying pulses to said reset pulse input, at a lower frequency.

3. Apparatus as in claim 1, in which the capacitor is shunted by a resistance, and said means for producing a first electrical analog potential comprises:
   (a) a relatively high frequency oscillator;
   (b) a frequency divider supplied by said oscillator and having a first output at a relatively low frequency, and a second output of sampling pulses spanning the midpoints of alternate half-cycles of the first output and having a duration substantially shorter than said half-cycles;
   (c) a square wave shaper connected to said first output for producing a square wave of fixed positive and negative excursions;
   (d) integrator means connected to the output of the shaper for producing a triangular electrical potential of said low frequency;
   (e) means for impressing said triangular wave across the capacitor and its shunting resistance to produce an output current equal to the sum of a triangular current through the resistance and a square wave current through the capacitor; and
   (f) means for sampling said output current at intervals determined by the sampling pulses from the frequency divider to produce an analog output signal varying with the capacitance and independent of the resistance of the resistor; and
   (g) means for storing said analog output signals between sampling pulses to produce said first electrical analog potential across said storing means.

4. Apparatus for measuring the capacitance of a capacitor while it is shunted by a resistor, comprising:
   (a) a relatively high frequency oscillator;
   (b) a frequency divider supplied by said oscillator and having a first output at a relatively low frequency, and a second output of sampling pulses spanning the midpoints of alternate half-cycles of the first output and having a duration substantially shorter than said half-cycles;
   (c) a square wave shaper connected to said first output for producing a square wave of fixed positive and negative excursions;
   (d) integrator means connected to the output of the shaper for producing a triangular electrical potential of said low frequency;
   (e) means for impressing said triangular wave across the capacitor and its shunting resistor to produce an output current equal to the sum of triangular current through the resistor and a square wave current through the capacitor; and
   (f) means for sampling said output current at intervals determined by the sampling pulses from the frequency divider to produce an analog output signal varying with the capacitance and independent of the resistance of the resistor.

5. Apparatus as in claim 4, including:
(a) an analog-to-digital converter having a digital counting pulse input and a reset pulse input;
(b) means in said frequency divider for supplying pulses to said digital counting pulse input at a preselected frequency and for supplying pulses to the reset pulse input at a substantially lower frequency.

6. Apparatus for measuring an unknown electrical resistance of at least one-tenth megohm, comprising:
(a) means for supplying a constant current;
(b) a resistor having a known resistance much smaller than said unknown resistance;
(c) a series circuit including said source, said unknown resistance and said known resistor, so that the current in said circuit varies inversely as the unknown resistance;
(d) an analog-to-digital converter having a divisor analog input, a dividend analog input, and a quotient digital output;
(e) means for supplying an analog potential varying directly with said current to the divisor input; and
(f) means for supplying a reference analog potential to the dividend input, so that the converter produces at the quotient output a digital signal varying directly with said resistance.

7. Apparatus as in claim 6, in which said converter also has a digital counting pulse input and a reset pulse input, said apparatus including:
(a) readout means with plural order digit displays;
(b) means responsive to the appearance of either all maxima or all minima on said plural order displays to produce a signal indicating that the range should be corrected;
(c) an oscillator for supplying timing pulses to the digital counting pulse input of the digital converter;
(d) frequency divider means for supplying pulses to the reset pulse input of the digital converter at a substantially lower frequency; and
(e) means in said frequency divider for controlling the flashing of said signal at a visually perceptible rate.

8. Apparatus as in claim 7, including range adjustment means for changing the significance of the digital orders in the readout means, so as to convert an all maxima or an all minimum display to a higher or lower display in which each order of the displays has a different digital significance.

* * * * *